United States Patent
Company et al.

(10) Patent No.: US 7,456,144 B2
(45) Date of Patent: Nov. 25, 2008

(54) PHOSPHATED ALCANOL, ITS USE AS A HYDROTROPE AND CLEANING COMPOSITION CONTAINING THE COMPOUND

(75) Inventors: Mahnaz Company, Hisingsbacka (SE); Magnus Franck, Onsala (SE); Anette Thyberg, Stenungsund (SE)

(73) Assignee: Akzo Nobel N.V., Arnhem (NL)

( * ) Notice: Subject to any disclaimer, the term of this patent is extended or adjusted under 35 U.S.C. 154(b) by 116 days.

(21) Appl. No.: 11/632,380

(22) PCT Filed: Jul. 8, 2005

(86) PCT No.: PCT/EP2005/053267

§ 371 (c)(1),
(2), (4) Date: Feb. 7, 2007

(87) PCT Pub. No.: WO2006/005721

PCT Pub. Date: Jan. 19, 2006

(65) Prior Publication Data

US 2007/0203048 A1   Aug. 30, 2007

Related U.S. Application Data

(60) Provisional application No. 60/608,167, filed on Sep. 8, 2004.

(30) Foreign Application Priority Data

Jul. 15, 2004   (EP)   ................... 04077043

(51) Int. Cl.
| | | |
|---|---|---|
| C11D 1/72 | (2006.01) | |
| C11D 3/36 | (2006.01) | |
| C11D 3/37 | (2006.01) | |
| C11D 7/06 | (2006.01) | |

(52) U.S. Cl. ........................ 510/467; 510/189; 510/222; 510/225; 510/228; 510/272; 510/413; 510/421; 510/423

(58) Field of Classification Search ................ 510/189, 510/222, 225, 228, 272, 413, 421, 423, 467
See application file for complete search history.

(56) References Cited

U.S. PATENT DOCUMENTS

| 3,294,693 A | 12/1966 | Dupre et al. ................. 252/135 |
|---|---|---|
| 4,137,190 A | 1/1979 | Chakrabarti et al. ...... 252/89 R |
| 4,493,782 A | 1/1985 | Williamson .................. 252/95 |
| 4,986,851 A * | 1/1991 | Dietz et al. .................. 106/503 |
| 5,145,597 A | 9/1992 | Rodriguez et al. .......... 252/135 |
| 2005/0181967 A1 | 8/2005 | Ruland et al. ............... 510/421 |

FOREIGN PATENT DOCUMENTS

| BE | 632 444 | 11/1963 |
|---|---|---|
| CH | 481 953 A | 11/1969 |
| EP | 0 256 427 A2 | 2/1988 |
| GB | 1142425 | 2/1969 |
| WO | WO 94/11331 | 5/1994 |
| WO | WO 03/091191 A1 | 11/2003 |

OTHER PUBLICATIONS

International Search Report for International Application No. PCT/EP2005/053267, Sep. 6, 2005.
Linfield et al. "Anionic Surfactants," Surfactant Science Series, vol. 7, Part II, pp. 504-511 (1976), no month given.

* cited by examiner

*Primary Examiner*—Brian P Mruk
(74) *Attorney, Agent, or Firm*—Ralph J. Mancini

(57) ABSTRACT

The present invention relates to the use of phosphated 2-propylheptanol or a phosphated 2-propylheptanol alkoxylate as a hydrotrope in aqueous alkaline solutions for a $C_8$-$C_{18}$-alcohol alkoxylate containing 1-20 ethyleneoxy units. It also relates to a phosphated 2-propylheptanol alkoxylate per se, and an alkaline cleaning composition comprising a $C_8$-$C_{18}$-alcohol alkoxylate containing 1-20 ethyleneoxy units and phosphated 2-propylheptanol and/or a phosphated 2-propylheptanol alkoxylate as a hydrotrope. The cleaning compositions may be used for industrial cleaning of hard surfaces, for example for vehicle cleaning or machine dishwashing.

11 Claims, No Drawings

PHOSPHATED ALCANOL, ITS USE AS A HYDROTROPE AND CLEANING COMPOSITION CONTAINING THE COMPOUND

The present invention relates to the use of phosphated 2-propylheptanol or a phosphated 2-propylheptanol alkoxylate as a hydrotrope in aqueous alkaline solutions for a $C_8$-$C_{18}$-alcohol alkoxylate containing 1-20 ethyleneoxy units. It also relates to a phosphated 2-propylheptanol alkoxylate per se and an alkaline cleaning composition comprising phosphated 2-propylheptanol and/or a phosphated 2-propylheptanol alkoxylate as a hydrotrope.

The ability of an aqueous solution to spread evenly over a surface, the so-called wetting ability, is important for many applications. For example, a composition for the cleaning of hard surfaces benefits from a good wetting of the surface. Good wetting is also desirable for laundry as well as for scouring and mercerizing processes. Nonionic surfactants are known to be good wetting agents, and are often present in compositions for the cleaning of hard surfaces. Most often the hard surface cleaning composition also contains alkaline components. Many nonionic surfactants are not soluble enough in solutions with a high amount of electrolytes, such as alkali and/or alkaline complexing agents, and therefore need the presence of a hydrotrope to improve the solubility. A number of hydrotropes for nonionic surfactants have been described in various publications. Examples of such hydrotropes are ethanol, sodium xylene sulphonate, sodium cumene sulphonate, alkyl glycosides, and phosphated alkoxylated alcohols.

In U.S. Pat. No. 5,145,597 alkaline cleaners useful in the cleaning of mechanical equipment are described. These alkaline cleaners include a phosphate ester hydrotrope and a nonionic surfactant, but in the working example it is not specified which phosphate ester is used.

U.S. Pat. No. 4,493,782 describes a cleansing composition containing an ethoxylated phosphate ester derived from an alcohol with between 8 and 12 carbon atoms in the alkyl chain, which alcohol has been ethoxylated with 2-4 moles of ethylene oxide (EO). This phosphate ester is combined with another phosphate ester prepared from butanol+2 EO, where the latter phosphate ester is added to stabilise the formulation.

U.S. Pat. No. 4,137,190 discloses a detergent composition comprising a nonionic surfactant and a synergistic hydrotrope mixture. In the working examples use is made of a combination of $P_2O_5$ phosphated phenol+6 EO and PPA phosphated butanol+1 EO or PPA phosphated isoamyl alcohol+4 EO.

U.S. Pat. No. 3,294,693 discloses hydrotropes for solubilising polyethylene oxide nonionic surfactants into builder solutions. The hydrotropes are surface-active materials which contain upwards of 85% primary phosphate esters. These esters are formed by the reaction between PPA and an ethoxylated $C_6$ to $C_{10}$ alkyl phenol or an ethoxylated $C_{10}$ to $C_{18}$ alcohol with 1-20 moles of EO. In all the working examples phosphated octylphenol ethoxylates were used.

BE 632 444 relates to alkaline detergents comprising surface-active nonionic polyethylene oxide adducts, obtained by the addition of ethylene oxide to an alcohol, an alkylamine or an alkylphenol, and a hydrotrope which is a phosphate of an alkoxylated alkylphenol having 6-10 carbon atoms in the alkyl group, or a phosphate of an alkoxylated alcohol having 10-18 carbon atoms in the alkyl chain, and where the hydrotropic material contains 90% primary phosphate esters. In the working examples several phosphated alkoxylated alkylphenols were used as hydrotropes, as well as phosphated dodecylalcohol+15 EO and phosphated stearylalcohol+7.5 EO, to solubilise octylphenol+10 EO.

Orthophosphoric acid esters produced from alcohols that have been ethoxylated with up to 10, preferably 5, moles of ethylene oxide are disclosed in EP-A-256427 as dispersants for pigments. 2-Propylheptanol is among the alcohols mentioned.

Alkali metal salts of mono- and diesters of orthophosphoric acid, produced from a number of alcohols, are disclosed in CH-A-481953 as surface-active agents used in a process for making a stable latex by emulsion polymerisation of vinylhalide monomers. Propylheptyl is mentioned as one possible alkyl substitutent in these phosphates.

However, there is still a need for new efficient hydrotropes that are suitable for certain compositions, since not all hydrotropes and nonionics are compatible for the achievement of clear, stable solutions and an optimal performance in the application at hand. Especially, in some cases alkaline solutions containing a nonionic surfactant obtained from an alkyl-branched alkoxylated alcohol and a hydrotrope will separate upon dilution. An example of such alcohol alkoxylates are 2-propylheptanol alkoxylates, where tests have shown that clear and homogeneous, alkaline concentrates, containing alkylene oxide adducts of 2-propylheptanol, and hexyl glucoside and/or an octyliminodipropionate as a hydrotrope, will become hazy or separate when they are diluted to make ready-to-use solutions.

The aim of the present invention is to find a new hydrotrope that is efficient in making clear homogeneous concentrated alkaline compositions containing $C_8$-$C_{18}$-alcohol alkoxylates comprising 1-20 ethyleneoxy units, especially 2-propylheptanol alkoxylates, which compositions will remain homogeneous upon dilution, and where the cleaning performance of the compositions is good.

It has now surprisingly been found that phosphated 2-propylheptanol or a phosphated 2-propylheptanol alkoxylate where the alkoxylate on the average comprises 1-20, preferably 2-10, more preferably 2-6, even more preferably 2-4, and most preferably 3, ethyleneoxy units and 0-3, preferably 0-2, propyleneoxy and/or butyleneoxy, preferably propyleneoxy, units, is an efficient hydrotrope in an alkaline aqueous solution for $C_8$-$C_{18}$, preferably $C_8$-$C_{12}$, alcohol alkoxylates containing 1-20, preferably 1-8, and most preferably 2-7 ethyleneoxy units and 0-3, preferably 0-2 propyleneoxy units, preferably for 2-propylheptanol alkoxylates according to the formula

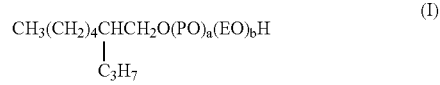

(I)

where PO is a propyleneoxy group, EO is an ethyleneoxy group, a is a number 0-3, and b is a number 1-8.

The invention further relates to aqueous cleaning solutions comprising a) 0.2-20%, preferably 2-10%, by weight of a $C_8$-$C_{18}$, preferably $C_8$-$C_{12}$, alcohol alkoxylate containing 1-20, preferably 1-8, and most preferably 2-7, ethyleneoxy units, preferably a 2-propylheptanol alkoxylate having the formula

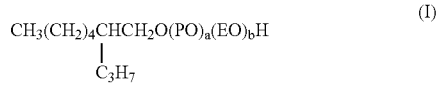

where EO, PO, a, and b have the same meaning as above b) 0.1-30, preferably 0.1-20, and most preferably 0.1-10% by weight of phosphated 2-propylheptanol and/or a phosphated 2-propylheptanol alkoxylate, where the alkoxylate on average comprises 1-20, preferably 2-10, more preferably 2-6, even more preferably 2-4, and most preferably 3, ethyleneoxy units and 0-3, preferably 0-2, propyleneoxy units, preferably a phosphated alkoxylate according to the formula

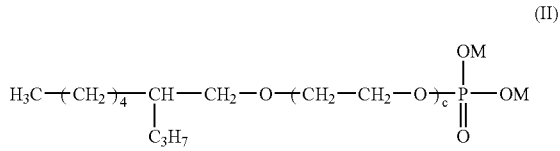

where M is H, a monovalent metal ion or $R_1R_2R_3R_4N^+$, where $R_1$, $R_2$, $R_3$, and $R_4$ are H, an alkyl group with 1-4 carbon atoms or —$CH_2CH_2OH$, and c is a number 1-20, preferably 2-10, more preferably 2-6, even more preferably 2-4, and most preferably 3, and c) 0.05-40, preferably 0.05-30, more preferably 0.05-20, and most preferably 0.05-15% by weight of an alkali hydroxide and/or alkaline complexing agents;

which are homogeneous and stable, also upon dilution. The cleaning performance of these solutions is also very good.

Phosphated 2-propylheptanol or a phosphated 2-propylheptanol alkoxylate may be obtained by different processes, the most common being the reaction of 2-propylheptanol or alkoxylated 2-propylheptanol with polyphosphoric acid or phosphorous pentoxide ($P_2O_5$).

In the process using polyphosphoric acid the resulting product mixture will predominantly contain the monoalkylphosphate ester of 2-propylheptanol or of alkoxylated 2-propylheptanol and only a small amount (<10%) of the dialkylphosphate ester. Always rather large amounts of inorganic phosphate residues from the polyphosphoric acid, such as orthophosphoric acid, will be present.

When $P_2O_5$ is used as the phosphatising reagent and the molar ratio between $P_2O_5$ and alcohol or alkoxylated alcohol is 1:3, the product mixture will contain about equal amounts of monoalkylphosphate ester and dialkylphosphate ester, and only smaller amounts of inorganic phosphate residues. A larger amount of alcohol or alkoxylated alcohol will yield more diester, and a smaller amount will yield more monoester. It will be known to a person skilled in the art how to synthesise phosphate esters with certain amounts of monoand dialkyl phosphate esters. For a general description of phosphate esters see, e.g., *Anionic Surfactants* Vol. 7, Part II, pages 504-511 in *Surfactant Science Series*, edited by Warner M. Linfield, Marcel Dekker Inc., New York and Basle 1976. The alcohol alkoxylates to be phosphated may be either of the standard type produced by using an alkaline catalyst such as KOH, or of the narrow range type produced by using a narrow range catalyst, such as an acid catalyst, $Ca(OH)_2$ or hydrotalcite.

Normally the reaction mixture resulting from either of the procedures will be neutralised by an organic or inorganic base before use. The base may be, e.g., an alkali hydroxide, such as sodium hydroxide or potassium hydroxide; ammonia, an alkanolamine, such as monoethanolamine, triethanolamine or methyldiethanolamine; or an alkylamine such as triethylamine.

The monoalkylphosphate ester of 2-propylheptanol or of ethoxylated 2-propylheptanol has the formula

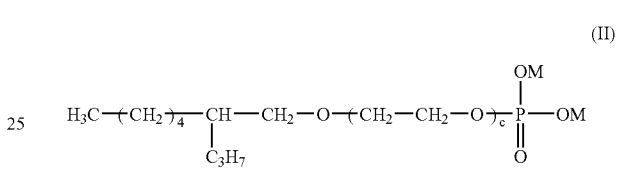

where M is H, a monovalent metal ion or $R_1R_2R_3R_4N^+$, where $R_1$, $R_2$, $R_3$, and $R_4$ are H, an alkyl group with 1-4 carbon atoms or —$CH_2CH_2OH$, and c is a number 0-20, preferably 2-10, more preferably 2-6, even more preferably 2-4, and most preferably 3. The product mixture resulting from the reaction of 2-propylheptanol or of ethoxylated 2-propylheptanol with polyphosphoric acid may also contain smaller amounts of products containing more than one phosphate unit according to the formula

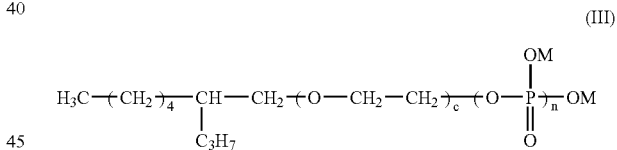

where n is 1-3 and M and c have the same meaning as above.

For ethoxylates containing smaller amounts of ethyleneoxy units, also a certain amount of unethoxylated product will remain due to the distribution of ethyleneoxy units. This unethoxylated product will also be phosphatised during the reaction with the phosphatising agent, and thus the phosphate ester of 2-propylheptanol will also be present in the reaction mixture resulting from these above-mentioned ethoxylates.

The dialkylphosphate ester of 2-propylheptanol has the formula

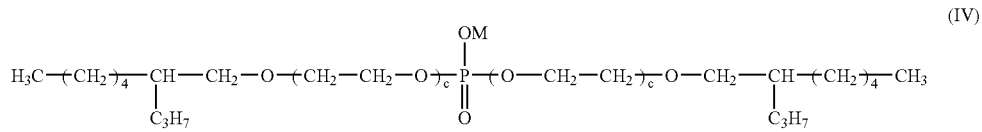

where M and c have the same meaning as above. The product mixture resulting from the reaction of 2-propylheptanol or ethoxylated 2-propylheptanol with $P_2O_5$ may also contain a dialkyl diphosphate ester according to the formula

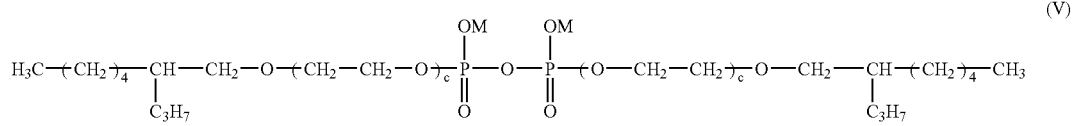

(V)

where M and c have the same meaning as above. This type of diester may be hydrolysed to yield 2 moles of monoester.

2-Propylheptanol is normally made by a process resulting in small amounts of by-products such as 4-methyl-2-propylhexanol and 5-methyl-2-propylhexanol. These products or their ethoxylates will also be phosphated during the process, and the phosphated species will be comprised in the resulting product mixture.

The reaction mixtures obtained by the phosphatising procedures are normally used as such without any purification procedure, but both the mixtures and the purified phosphate esters function as hydrotropes. To act as a good hydrotrope, the mixture should predominantly contain the monoalkyl phosphate esters, since these are better hydrotropes than the dialkyl phosphate esters. Preferably more than 60, more preferably more than 70, and most preferably more than 80% by weight of the mixture should be monoalkyl phosphate esters.

The phosphated 2-propylheptanol or phosphated 2-propylheptanol alkoxylates where the alkoxylate on average comprises 1-20, preferably 2-10, more preferably 2-6, even more preferably 2-4, and most preferably 3, ethyleneoxy units and 0-3, preferably 0-2, propyleneoxy and/or butyleneoxy, preferably propyleneoxy, units described above and a process for their production are already partly disclosed in the earlier mentioned publications EP-A-256427 and CH-A-481953 for use as dispersants for pigments and as additives in an emulsion polymerisation process, respectively. However, the phosphated 2-propylheptanol alkoxylate where the alkoxylate comprises 2-4, preferably 3, ethyleneoxy units on average is especially efficient as a hydrotrope compared to the other phosphated alkoxylates of 2-propylheptanol (see Table 1 in the Examples). Therefore, the invention also relates to the phosphated 2-propylheptanol alkoxylate where the alkoxylate on average comprises 2-4, preferably 3, ethyleneoxy units per se and a process for its production.

The $C_8$-$C_{18}$-alcohol alkoxylates may, in addition to the 1-20 ethyleneoxy units, also contain 1-3 alkyleneoxy units with 3-4 carbon atoms. The ethyleneoxy units and the propyleneoxy and/or butyleneoxy units may be added randomly or in blocks. The blocks may be added to the alcohol in any order. The alkoxylates may also contain an alkyl group with 1-4 carbon atoms in the end position. Preferably, the alkoxylates contain 2-7 ethyleneoxy units and 0-2 propyleneoxy and/or butyleneoxy units.

A suitable alkoxylate to be used in the cleaning composition for the cleaning of hard surfaces has the formula

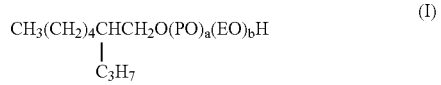

(I)

where PO is a propyleneoxy group, EO is an ethyleneoxy group, a is a number 0-3, preferably 0-2, and b is a number 1-8, preferably 2-7, and most preferably 3-6. When the 2-propylheptanol contains the by-products mentioned above, these will also be alkoxylated and comprised in the resulting product mixture. The cleaning concentrates obtained by using the phosphated 2-propylheptanol alkoxylates as hydrotropes for the 2-propylheptanol alkoxylates are clear and stable, also upon dilution, and cleaning compositions with these components exhibit a good cleaning performance.

When the cleaning composition is to be used for textile applications, such as for laundry, then the alkoxylate a) should preferably comprise an amount of ethyleneoxy units in the upper part of the range 1-20, for example 7-15 moles of EO per mole of $C_8$-$C_{18}$-alcohol.

The alkali hydroxide in the composition preferably is sodium or potassium hydroxide. The alkaline complexing agent may be inorganic as well as organic. Typical examples of inorganic complexing agents used in the alkaline composition are alkali salts of silicates and phosphates such as sodium silicate, sodium metasilicate, sodium tripolyphosphate, sodium orthophosphate, sodium pyrophosphate, and the corresponding potassium salts. Typical examples of organic complexing agents are alkaline aminopolyphosphonates, organic phosphates, polycarboxylates, such as citrates; aminocarboxylates, such as sodium nitrilotriacetate ($Na_3NTA$), sodium ethylenediaminetetraacetate (EDTA), sodium diethylenetriaminepentaacetate, sodium 1,3-propylenediamine-tetraacetate, and sodium hydroxyethylethylenediaminetriacetate. The amount of alkali present in the composition depends on the application and on whether the composition is a concentrate or a ready-to-use solution. Some applications use highly alkaline solutions; for example for scouring, the alkali concentration is c. 4-6% by weight when using NaOH, and for mercerization, a ca. 20-26% by weight caustic soda solution is used. A concentrate composition for vehicle cleaning normally contains 6% to 15% by weight alkali and/or alkaline complexing agents, and the ready-to-use solution normally contains 0.2 to 5% by weight. For laundry, the amount of alkali and/or alkaline complexing agents is lower and normally amounts to 3 to 10% by weight in the concentrate and 0.1 to 1% by weight in the ready-to-use solution.

The concentrated compositions of the present invention are clear and stable. The clarity interval is suitably between 0-40° C., preferably between 0-50° C., and most preferably between 0-60° C. This may be adapted by changing the ratio of hydrotrope to nonionic surfactant. The concentrate normally contains 50-95% by weight of water, suitably 70-90% by weight.

To obtain a ready-to-use solution the concentrates are diluted with water up to 1:40. The diluted solutions are also clear and stable, but in some cases they may turn a little bit hazy although they are still stable and do not separate. The ready-to-use solutions exhibit good cleaning properties. A typical concentrate formulation for vehicle cleaning contains 3-5% by weight of a), 3-5% by weight of b), and 5-10% by weight of c), and a ready-to-use formulation would normally contain 0.2-1% by weight of a), 0.2-1% by weight of b), and 0.5-1% by weight of c).

The present invention is further illustrated by the following Examples.

EXAMPLE 1

Formulations were made containing:
5% by weight of a nonionic surfactant
10% by weight of Na$_3$NTA (sodium nitrilotriacetate)
X % by weight of hydrotrope
Balance Water The hydrotrope was added in such an amount that the solution exhibited the clarity interval stated in Table 2. All percentages are by weight.

TABLE 1

| Compound | I | II | III | IV (Comparison) | V | VI | VII |
|---|---|---|---|---|---|---|---|
| Phosphated 2-PH[1] | 4.4% | | | | 5.9% | | |
| Phosphated 2-PH + 3EO[2] | | 3.2% | | | | 4.2% | |
| Phosphated 2-PH + 5EO[3] | | | 5.4% | | | | 6.1% |
| Coco fatty amine + 17EO quaternised with CH$_3$Cl | | | | 3% | | | |
| C$_9$-C$_{11}$-alcohol + 4EO | 5% | 5% | 5% | 5% | | | |
| 2-PH + 5EO | | | | | 5% | 5% | 5% |

[1] 2-PH = 2-propylheptanol
[2] 2-PH + 3EO = 2-propylheptanol ethoxylated with 3 moles of ethylene oxide
[3] 2-PH + 5EO = 2-propylheptanol ethoxylated with 5 moles of ethylene oxide To evaluate the cleaning efficiency of the formulations in Table 1 the following cleaning test was used: White painted plates were smeared with an oil-soot mixture obtained from diesel engines. 25 ml of the test solutions, in this case the formulations in Table 1 diluted 1:20, were poured onto the top of the oil-smeared plates and left there for one minute. The plates were then rinsed off with a rich flow of water. All solutions and the water were kept at a temperature of about 15-20° C. All reference solutions were placed on the same plate as the test solutions. The cleaning ability was measured with a Minolta Chroma Meter CR-200 reflectometer, and the result is presented as the % soil removal. The results are collected in Table 2.

TABLE 2

| Formulation No | Clarity interval (° C.) | Appearance after dilution 1:20 | Soil removal at 1:20 dilution (%) |
|---|---|---|---|
| I | 0-50 | Hazy but stable | 77.5 |
| II | 0-46 | Clear | 83.0 |
| III | 0-45 | Clear | 81.0 |
| IV (comparison) | 0-80 | Clear | 69.5 |
| V | 0-75 | Hazy but stable | 71.5 |
| VI | 0-60 | Clear | 74.0 |
| VII | 0-60 | Clear | 73.5 |
| IV (comparison) | 0-80 | Clear | 63.0 |

The formulations containing phosphated 2-propylheptanol or phosphated 2-propylheptanol ethoxylates as a hydrotrope exhibited a better cleaning performance than the comparison formulation containing coco fatty amine+17 EO quaternised with CH$_3$Cl. There are two values for the comparison compound, since the cleaning efficiency was tested on two separate plates; one with I, II, III, and IV and the other with V, VI, VII, and IV.

EXAMPLE 2

This example relates to a comparison between phosphated 2-propylheptanol+5 EO and phosphated hexanol+5 EO as hydrotropes for 2-propylheptanol+5 EO.

TABLE 3

| Compound | Formulation A | Formulation B (Comparison) |
|---|---|---|
| Phosphated 2-PH + 5EO | 3.5% | |
| Phosphated hexanol + 5EO | | 4.9% |
| 2-PH + 5EO | 5.0% | 5.0% |
| Sodium metasilicate | 4.0% | 4.0% |
| Tetrapotassium pyrophosphate | 6.0% | 6.0% |
| Water | 81.5% | 80.1% |

TABLE 4

| Formulation | Clarity interval (° C.) | Appearance after dilution 1:1 | Appearance after dilution 1:5 | Appearance after dilution 1:10 | Appearance after dilution 1:20 | Soil removal at 1:20 dilution (%) |
|---|---|---|---|---|---|---|
| A | 0-60 | Clear | Clear | Hazy but stable | Hazy but stable | 68.5 |
| B (comp.) | 0-60 | Separated | Separated | Separated | Separated | 70.5 |
| IV (comp.) | 0-80 | Clear | Clear | Clear | Clear | 62.8 |

A smaller amount of phosphated 2-propylheptanol+5 EO, as compared to phosphated hexanol+5 EO, was required to obtain a clarity interval of 0-60° C.

The formulations with phosphated 2-propylheptanol+5 EO as a hydrotrope exhibited about the same cleaning efficiency as the formulations with phosphated hexanol+5 EO, but the former were much more stable when diluted than the latter.

EXAMPLE 3

This example compares a number of phosphated ethoxylated alcohols with phosphated 2-propylheptanol+5 EO as a hydrotrope for 2-propylheptanol+5 EO.

TABLE 5

| Compound | 1 | 2 (Comparison) | 3 (Comparison) | 4 (Comparison) |
|---|---|---|---|---|
| 2-PH + 5EO | 5.0% | 5.0% | 5.0% | 5.0% |
| Phosphated 2-PH + 5EO | 3.5% | | | |
| Phosphated $C_9$-$C_{11}$-alcohol + 5.5EO | | 3.0% | | |
| Phosphated $C_9$-$C_{11}$-alcohol + 4EO | | | 3.4% | |
| Phosphated 2-ethylhexanol + 4EO | | | | 3.0% |
| Sodium metasilicate | 4.0 | 4.0 | 4.0 | 4.0 |
| Tetrapotassium pyrophosphate | 6.0 | 6.0 | 6.0 | 6.0 |
| Water | 81.5 | 82.0 | 79.0 | 82.0 |

TABLE 6

| Formulation | Clarity interval (° C.) | Appearance after dilution 1:5 after 1 day | Appearance after dilution 1:20 after 1 day | Appearance after dilution 1:5 after 1 week | Appearance after dilution 1:20 after 1 week | Soil removal at 1:20 dilution (%) |
|---|---|---|---|---|---|---|
| 1 | 0-70 | Clear | Clear | Clear | Hazy but stable | 60.0 |
| 2 (Comp.) | 0-53 | Clear | Clear | Clear | Clear | 26.0 |
| 3 (Comp.) | 0-60 | Clear | Clear | Clear | Clear | 44.0 |
| 4 (Comp.) | 0-50 | Hazy | Hazy | Cloudy | Hazy | 54.0 |

The formulation according to the invention exhibited the best cleaning performance of all the investigated formulations, in combination with a good stability upon dilution.

EXAMPLE 4

Table 7 displays formulations where the same amount of hydrotrope was added to all formulations. The cleaning efficiency of the different formulations is shown in Table 8.

TABLE 7

| Compound | 5 | 6 | 7 (Comp.) | 8 (Comp.) | 9 (Comp.) |
|---|---|---|---|---|---|
| 2-PH + 5 EO | 5.0% | 5.0% | 5.0% | 5.0% | 5.0% |
| Phosphated 2-PH + 3 EO | 3.7% | | | | |
| Phosphated 2-PH + 5 EO | | 3.7% | | | |
| Phosphated $C_9$-$C_{11}$-alcohol + 5.5 EO | | | 3.7% | | |
| Phosphated $C_9$-$C_{11}$-alcohol + 4 EO | | | | 3.7% | |
| Phosphated 2-ethylhexanol + 4 EO | | | | | 3.7% |
| Sodium metasilicate | 4.0 | 4.0 | 4.0 | 4.0 | 4.0 |
| Tetrapotassium pyrophosphate | 6.0 | 6.0 | 6.0 | 6.0 | 6.0 |
| Water | 81.3 | 81.3 | 81.3 | 81.3 | 81.3 |

TABLE 8

| Formulation | Clarity interval (° C.) | Appearance after dilution 1:5 after 4 days | Appearance after dilution 1:20 after 4 days | Soil removal at 1:30 dilution (%) | Soil removal at 1:40 dilution (%) |
|---|---|---|---|---|---|
| 5 | >60 | Clear | Clear | 50.0 | 40.0 |
| 6 | 50 | Clear | Clear | 61.0 | 47.0 |
| 7 (Comp.) | 51 | Clear | Clear | 16.0 | 13.0 |
| 8 (Comp.) | >60 | Clear | Clear | 27.0 | 20.0 |
| 9 (Comp.) | >60 | Hazy | Hazy | 36.0 | 21.0 |

The formulations according to the invention are more efficient than the comparison formulations.

EXAMPLE 5

In this example phosphated 2-propylheptanol+5 EO was added as a hydrotrope to a number of nonionic surfactants, and the formulations were tested for their cleaning efficiency.

TABLE 9

| Compound | 10 | 11 | 12 | 13 |
|---|---|---|---|---|
| Phosphated 2-PH + 5EO | 5.5 | 2.8 | 2.5 | 2.3 |
| $C_9$-$C_{11}$-alcohol + | | 5.0 | | |

TABLE 9-continued

| Compound | 10 | 11 | 12 | 13 |
|---|---|---|---|---|
| 4EO | | | | |
| 2-ethyl-hexanol + 4EO | | 5.0 | | |
| $C_9$-$C_{11}$-alcohol + 5.5EO | | | 5.0 | |
| 2-ethylhexanol + 2PO + 4EO | | | | 5.0 |
| Sodium metasilicate | 4.0 | 4.0 | 4.0 | 4.0 |
| Tetrapotassium pyrophosphate | 6.0 | 6.0 | 6.0 | 6.0 |
| Water | 79.5 | 82.2 | 82.5 | 82.7 |

TABLE 10

| Formulation | Clarity interval (° C.) | Appearance after dilution 1:20 after 1 month | Soil removal at 1:20 dilution (%) |
|---|---|---|---|
| 10 | 0-45 | Clear | 71.0 |
| 11 | 0-50 | Clear | 41.0 |
| 12 | 0-49 | Clear | 65.0 |
| 13 | 0-50 | Slightly hazy but stable | 76.0 |

The results show that phosphated 2-propylheptanol+5 EO also works as a hydrotrope for other nonionics than 2-propylheptanol alkoxylates, and that the cleaning efficiency for these formulations in general is good.

EXAMPLE 6

In this example the wetting ability of a composition according to the invention was measured by the modified Drave's test.

TABLE 11

| Compound | C |
|---|---|
| Phosphated 2-PH + 5EO | 6% |
| $C_9$-$C_{11}$-alcohol + 4EO | 5.0% |
| Sodium nitrilotriacetate | 10.0% |

In the modified Drave's test, the sinking time in s is measured for a specified cotton yarn in approximately 0.1% surfactant solution. The formulation in the Table above was diluted with distilled water to 0.1% by weight with respect to the $C_9$-$C_{11}$-alcohol+4 EO, and the modified Drave's test was performed on this solution. The result is displayed in the Table below.

TABLE 12

| Formulation | Clarity interval (° C.) | pH | Sinking time (s) |
|---|---|---|---|
| C | 0-45 | 10.5 | 5 |

The formulation containing the phosphated 2-propylheptanol+5 EO as a hydrotrope for the ethoxylate had a good wetting ability, whereas for the different components alone, the wetting time was >420 s. The $C_9$-$C_{11}$-alcohol is not soluble in this alkaline medium without a hydrotrope, and the phosphated 2-propylheptanol+5 EO has no good wetting ability on its own. When the hydrotrope is added, the nonionic surfactant is solubilised, and it is then able to exert its wetting ability.

EXAMPLE 7

In the syntheses described below a 1,000 cm³ flange flask equipped with an anchor stirrer was used. The reactor was heated by an electrical heater equipped with a thermostat. A slight flow of nitrogen was applied during the reaction. The polyphosphoric acid (PPA) used was Polyphosphoric acid 116, 84% equivalent in $P_2O_5$ (Albright & Wilson).

1) 2-propylheptanol+PPA 2-propylheptanol (222.47 g, 1.41 mole) was charged and heated to 45° C. PPA (254.09 g) was added from a 60 ml syringe and the exothermic reaction was kept at 55-70° C. while stirring at 240 r/min. PPA was added during a period of 1 hour. The reaction was then left for 2 h at 60° C. and with stirring at 300 r/min. After the post-reaction water (5.0 g) was added to hydrolyse the remaining PPA, after which the acid was neutralised with KOH (274.4 g) dissolved in 555.0 g water.

2) 2-propylheptanol+3 EO+PPA 2-propylheptanol+3 EO (295.63 g, 1.02 mole) was charged and heated to 45° C. PPA (184.95 g) was added from a 60 ml syringe and the exothermic reaction was kept at 55-70° C. while stirring at 240 r/min. PPA was added during a period of 1 hour. The reaction was then left for 2 h at 60° C. and with stirring at 300 r/min. After the post-reaction water (5.0 g) was added to hydrolyse the remaining PPA, after which the acid was neutralised with KOH (191 g) dissolved in 454 g water.

3) 2-propylheptanol+5 EO+PPA 2-propylheptanol+5 EO (307.71 g, 0.81 mole) was charged and heated to 45° C. PPA (148 g) was added from a 60 ml syringe and the exothermic reaction was kept at 55-70° C. while stirring at 240 r/min. PPA was added during a period of 1 hour. The reaction was then left for 2 h at 60° C. and with stirring at 300 r/min. After the post reaction water (5.0 g) was added to hydrolyse the remaining PPA, after which 374.02 g acid were neutralised with KOH (132.37 g) dissolved in 517 g water.

What is claimed is:

1. An aqueous alkaline solution comprising phosphated 2-propylheptanol or a phosphated 2-propylheptanol alkoxylate, where the alkoxylate on average comprises 1 to 20 ethyleneoxy units and 0-3 propyleneoxy and/or butyleneoxy units, as a hydrotrope for a $C_8$-$C_{18}$ alcohol alkoxylate containing 1-20 ethyleneoxy units.

2. The solution of claim 1, wherein the $C_8$-$C_{18}$-alcohol alkoxylate has the formula

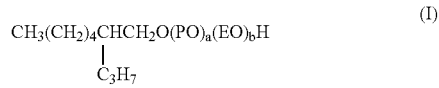
(I)

where PO is a propyleneoxy group, EO is an ethyleneoxy group, a is a number 0-3, and b is a number 1-8.

3. The solution of claim 1 wherein the phosphated 2-propylheptanol or the phosphated 2-propylheptanol alkoxylate has the formula

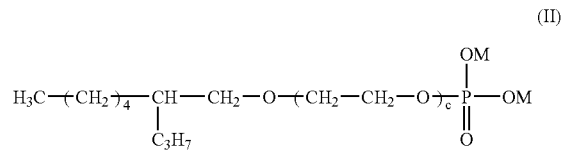
(II)

where M is H, a monovalent metal ion or $R_1R_2R_3R_4N^+$, where $R_1$, $R_2$, $R_3$, and $R_4$ are H, an alkyl group with 1-4 carbon atoms or —$CH_2CH_2OH$, and c is a number 0-20.

4. The solution of claim 3 wherein the phosphated alkoxylate is present in a mixture containing two or more of
compounds of formula II,
compounds of the formula

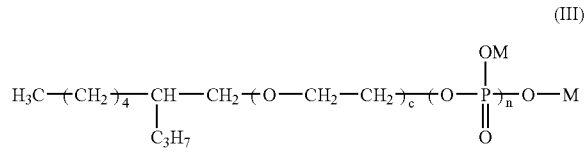
(III)

compounds of the formula

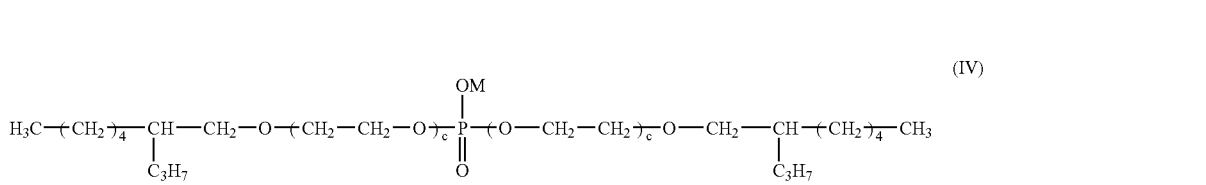
(IV)

compounds of the formula

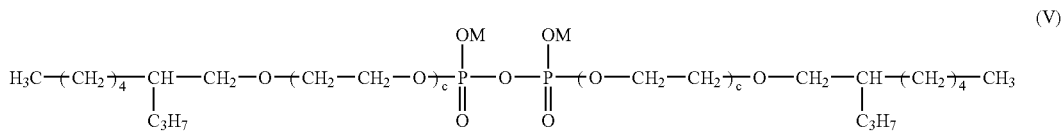
(V)

wherein in each of the formulae (III), (IV) and (V), M is H, a monovalent metal ion or $R_1R_2R_3R_4N^+$, where $R_1$, $R_2$, $R_3$, and $R_4$ are H, an alkyl group with 1-4 carbon atoms or —$CH_2CH_2OH$, and c is a number 0-20 n is 1-3, and where II is present in an amount of at least 60% by weight of the mixture.

5. A cleaning composition comprising a) 0.2-20% by weight of a $C_8$-$C_8$-alcohol alkoxylate containing 1-20 ethyleneoxy units
b) 0.1-30% by weight of phosphated 2-propylheptanol and/or a phosphated 2-propylheptanol alkoxylate, where the alkoxylate on average comprises 1 to 20 ethyleneoxy units and 0-3 propyleneoxy units, and
c) 0.05-40% by weight of an alkali hydroxide and/or alkaline complexing agents.

6. A composition according to claim 5, where a) is an alcohol alkoxylate comprising 2-7 ethyleneoxy units and b) is a phosphated 2-propylheptanol alkoxylate comprising 2-4 ethyleneoxy units.

7. The composition of claim 5 wherein -b) comprises phosphated 2-propylheptanol and/or one or more phosphated 2-propylheptanol alkoxylates having the formulae II, III, IV and/or V, wherein formula II
has the formula

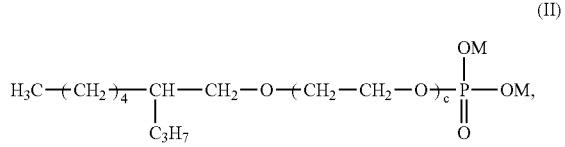
(II)

formula III has the formula

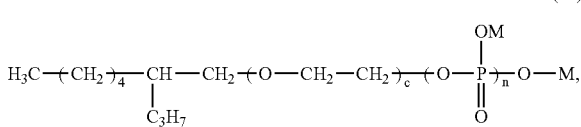
(III)

formula IV has the formula

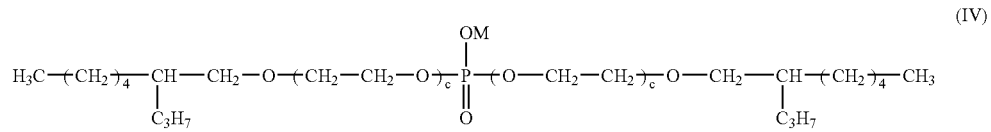
(IV)

and formula V has the formula

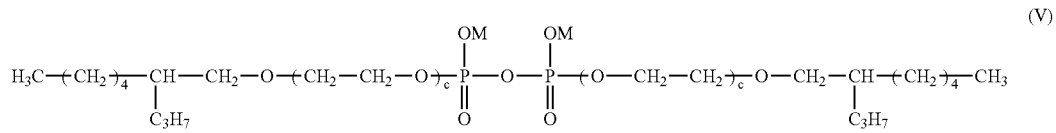

wherein in each of formulae (II), (III), (IV), and (V), M is H, a monovalent metal ion or $R_1R_2R_3R_4N^+$, where $R_1$, $R_2$, $R_3$ and $R_4$ are H, an alkyl group with 1-4 carbon atoms or —$CH_2CH_2OH$, c is a number 0-20, and n is 1-3, and where II is present in an amount of at least 80% by weight of the mixture.

8. The composition claim 5 wherein -b) is a 2-propylheptanol alkoxylate according to formula (I), wherein formula I has the formula

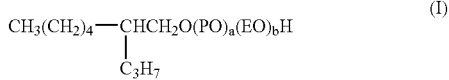

wherein a is 0 and b is on average 3-6.

9. An industrial hard surface cleaner comprising the composition of claim 5.

10. A dishwashing detergent comprising the composition of claim 5.

11. A vehicle cleaning composition comprising the composition of claim 5.

* * * * *

UNITED STATES PATENT AND TRADEMARK OFFICE
CERTIFICATE OF CORRECTION

| | | |
|---|---|---|
| PATENT NO. | : 7,456,144 B2 | |
| APPLICATION NO. | : 11/632380 | |
| DATED | : November 25, 2008 | |
| INVENTOR(S) | : Mahnaz Company, Magnus Franck and Anette Thyberg | |

It is certified that error appears in the above-identified patent and that said Letters Patent is hereby corrected as shown below:

Col. 13, line 48,    change "$C_8$-$C_8$-alcohol"

to --$C_8$-$C_{18}$-alcohol--

Signed and Sealed this
Thirty-first Day of May, 2011

David J. Kappos
*Director of the United States Patent and Trademark Office*